[12] United States Patent
Wood

(10) Patent No.: US 9,316,602 B2
(45) Date of Patent: *Apr. 19, 2016

(54) X-RAY BACKSCATTER DETECTION USING MODULATED X-RAYS

(71) Applicant: Lockheed Martin Corporation, Bethesda, MD (US)

(72) Inventor: J. Richard Wood, Grapevine, TX (US)

(73) Assignee: Lockheed Martin Corporation, Bethesda, MD (US)

(*) Notice: Subject to any disclaimer, the term of this patent is extended or adjusted under 35 U.S.C. 154(b) by 126 days.

This patent is subject to a terminal disclaimer.

(21) Appl. No.: 14/158,152

(22) Filed: Jan. 17, 2014

(65) Prior Publication Data

US 2014/0133631 A1   May 15, 2014

Related U.S. Application Data

(63) Continuation-in-part of application No. PCT/US2012/067217, filed on Nov. 30, 2012.

(60) Provisional application No. 61/566,584, filed on Dec. 2, 2011.

(51) Int. Cl.
| G01N 23/203 | (2006.01) |
| G01V 5/00 | (2006.01) |
| G01N 23/20 | (2006.01) |
| G21K 1/00 | (2006.01) |

(52) U.S. Cl.
CPC ........ *G01N 23/203* (2013.01); *G01N 23/20008* (2013.01); *G01V 5/0025* (2013.01); *G21K 1/00* (2013.01); *G01N 2223/053* (2013.01)

(58) Field of Classification Search
CPC ............. A61B 6/483; G01N 23/20058; G01N 23/203; G01N 2223/053; G01N 2223/056; G01N 2223/0566; G01N 2223/304; G01N 2223/345; G01N 2223/41; G01N 2223/425; G01N 2223/426; G01N 2223/625; G01N 2223/626; G01N 2223/639; G01V 5/0008; G01V 5/0016; G01V 5/0025

See application file for complete search history.

(56) References Cited

U.S. PATENT DOCUMENTS

| 4,035,616 A | 7/1977 | Piringer |
| 4,385,549 A | 5/1983 | Bauer et al. |

(Continued)

FOREIGN PATENT DOCUMENTS

| JP | 5142396 A | 6/1993 |
| WO | 2013082374 A1 | 6/2013 |

OTHER PUBLICATIONS

Notice of Allowance and Examiner-Initiated Interview Summary for U.S. Appl. No. 13/368,257, mailed Oct. 31, 2014, 9 pages.

(Continued)

*Primary Examiner* — Thomas R Artman
(74) *Attorney, Agent, or Firm* — Withrow & Terranova, PLLC

(57) ABSTRACT

Mechanisms for identifying a characteristic of a material. An X-ray signal is generated. The X-ray signal is modulated with at least two radio frequency modulation signals to form a modulated X-ray signal. The modulated X-ray signal is directed toward a target material. A backscatter signal is received from the target material, the backscatter signal including harmonic components generated by the target material in response to receiving the modulated X-ray signal. Based at least in part on the harmonic components, a characteristic of the target material is identified.

22 Claims, 6 Drawing Sheets

(56) References Cited

U.S. PATENT DOCUMENTS

| | | | |
|---|---|---|---|
| 4,881,549 A * | 11/1989 | Rhyne | 600/443 |
| 4,935,616 A | 6/1990 | Scott | |
| 5,044,006 A | 8/1991 | Cyrulnik | |
| 5,206,592 A | 4/1993 | Buess et al. | |
| 5,592,083 A | 1/1997 | Magnuson et al. | |
| 5,608,403 A | 3/1997 | Miller | |
| 5,635,721 A | 6/1997 | Bardi et al. | |
| 5,642,393 A | 6/1997 | Krug et al. | |
| 5,696,577 A | 12/1997 | Stettner et al. | |
| 5,751,830 A | 5/1998 | Hutchinson | |
| 5,754,290 A | 5/1998 | Rajic et al. | |
| 5,760,403 A | 6/1998 | Elabd | |
| 6,088,423 A | 7/2000 | Krug et al. | |
| 6,194,898 B1 | 2/2001 | Magnuson et al. | |
| 6,531,225 B1 | 3/2003 | Homme et al. | |
| 6,544,458 B1 * | 4/2003 | Hansma | 264/234 |
| 6,762,420 B2 | 7/2004 | Homme et al. | |
| 6,952,163 B2 | 10/2005 | Huey et al. | |
| 7,023,956 B2 | 4/2006 | Heaton et al. | |
| 7,130,371 B2 | 10/2006 | Elyan et al. | |
| 7,135,672 B2 | 11/2006 | Land | |
| 7,142,109 B1 | 11/2006 | Frank | |
| 7,231,017 B2 | 6/2007 | Gertsenshteyn et al. | |
| 7,317,390 B2 | 1/2008 | Huey et al. | |
| 7,327,137 B1 | 2/2008 | Crowley et al. | |
| 7,344,304 B2 | 3/2008 | Hardesty | |
| 7,368,292 B2 | 5/2008 | Hummel et al. | |
| 7,385,549 B2 | 6/2008 | Lovberg et al. | |
| 7,433,054 B1 | 10/2008 | Tischhauser et al. | |
| 7,453,552 B1 | 11/2008 | Miesak | |
| 7,646,851 B2 | 1/2010 | Liu et al. | |
| 8,111,808 B1 | 2/2012 | Wood | |
| 8,411,820 B1 | 4/2013 | Browder et al. | |
| 8,411,821 B1 | 4/2013 | Wood et al. | |
| 8,433,037 B1 | 4/2013 | Wood | |
| 8,983,034 B2 * | 3/2015 | Wood | 378/87 |
| 2003/0144800 A1 | 7/2003 | Davis et al. | |
| 2004/0165187 A1 | 8/2004 | Koo et al. | |
| 2004/0257224 A1 | 12/2004 | Sajkowsky | |
| 2005/0079386 A1 | 4/2005 | Brown, Jr. et al. | |
| 2005/0099292 A1 | 5/2005 | Sajkowsky | |
| 2005/0104603 A1 | 5/2005 | Peschmann et al. | |
| 2006/0022140 A1 | 2/2006 | Connelly et al. | |
| 2006/0145812 A1 | 7/2006 | Sajkowsky | |
| 2007/0008135 A1 | 1/2007 | Sajkowsky | |
| 2007/0025512 A1 | 2/2007 | Gertsenshteyn et al. | |
| 2007/0211922 A1 | 9/2007 | Crowley et al. | |
| 2008/0111545 A1 | 5/2008 | Crowley | |
| 2008/0120430 A1 | 5/2008 | Redmond | |
| 2012/0141009 A1 * | 6/2012 | Wood | 382/132 |
| 2014/0133631 A1 * | 5/2014 | Wood | 378/88 |
| 2014/0355741 A1 * | 12/2014 | Wood | 378/86 |
| 2015/0168137 A1 * | 6/2015 | Pauly | 378/70 |

OTHER PUBLICATIONS

Carter et al., "A Microchannel Plate Intensified, Subnanosecond, X-ray Imaging Camera," Physica Scripta, vol. 41, pp. 390-395, 1990.
Notice of Allowance for U.S. Appl. No. 12/541,539 mailed Sep. 28, 2011, 8 pages.
Non-final Office Action for U.S. Appl. No. 12/541,539 mailed Feb. 10, 2011, 8 pages.
Kozyrev, A.B. et al., "Nonlinear Behavior of Thin Film SrTiO3 Capacitors at Microwave Frequencies," Journal of Applied Physics, vol. 84, Issue 6, Sep. 1998, American Institute of Physics, pp. 3326-3332.
Runkle, Robert C. et al., "Photon and neutron interrogation techniques for chemical explosives detection in air cargo: A critical review," Nuclear Instruments and Methods in Physics Research, Section A: Accelerators, Spectrometers, Detectors and Associated Equipment, vol. 603, Issue 3, May 21, 2009, Elsevier B.V., pp. 510-528.
Yu, Y.H. et al., "Measurement of Thin Film Piezoelectric Constants Using X-ray Diffraction Technique," Physica Scripta, vol. 2007, T129, Dec. 2007, IOP Publishing, pp. 353-357.
International Search Report and Written Opinion for PCT/US2012/067217, mailed Mar. 28, 2013, 14 pages.
International Preliminary Report on Patentability and Written Opinion for PCT/US2012/067217, mailed Jun. 12, 2014, 8 pages.
Non-final Rejection for for U.S. Appl. No. 12/604,548, mailed Feb. 22, 2011, 11 pages.
Final Office Action for U.S. Appl. No. 12/604,548, mailed Jun. 3, 2011, 11 pages.
Non-final Rejection for U.S. Appl. No. 12/604,548, mailed Oct. 25, 2012, 11 pages.
Notice of Allowance for U.S. Appl. No. 12/604,548, mailed Feb. 8, 2013, 5 pages.
Non-Final Office Action for U.S. Appl. No. 13/368,257, mailed Mar. 27, 2014, 4 pages.
Notice of Allowance for U.S. Appl. No. 13/368,257, mailed Jul. 18, 2014, 9 pages.
Notice of Allowance for U.S. Appl. No. 14/362,276, mailed Aug. 13, 2015, 8 pages.
Corrected Notice of Allowance for U.S Appl. No. 14/362,276, mailed Nov. 18, 2015, 4 pages.

* cited by examiner

X-RAY BACKSCATTER DETECTION USING MODULATED X-RAYS

RELATED APPLICATIONS

This application is a continuation-in-part of co-pending PCT Application No. PCT/US12/67217, filed on Nov. 30, 2012, entitled "X-RAY BACKSCATTER DETECTION USING RADIO FREQUENCY MODULATED INCIDENT X-RAYS," which claims the benefit of provisional Patent Application Ser. No. 61/566,584, filed on Dec. 2, 2011, entitled "MODULATED X-RAY HARMONIC DETECTION," the disclosures of which are hereby incorporated herein by reference in their entireties.

TECHNICAL FIELD

The embodiments relate to the analysis of materials, and in particular to the use of X-ray energy to analyze characteristics of materials.

BACKGROUND

Many molecular structures, when under stress, or when strained, may exhibit nonlinear movement if current can be caused to flow through or around the molecular structures. Thus, the ability to detect nonlinear movement of a molecular structure may facilitate identification of stress or strain in the molecular structure. The detection of stress or strain in a molecular structure may be useful for a variety of reasons. A metal structure under strain, for example, may identify a weak area that has a potential for catastrophic separation under certain conditions. As another example, an electronic memory may store a value, such as a logical one, via an electrical charge that results in strain on a semiconductor gate, or other semiconductor component. An ability to detect such strain in the electronic memory may facilitate reading the data stored in the electronic memory.

SUMMARY

The embodiments relate to mechanisms for causing current to flow about molecular structures, and for detecting nonlinear movements of such molecular structures in response to such current flow to identify characteristics of the material. In one embodiment, a method for identifying a characteristic of a material is provided. The method includes generating an X-ray signal, and modulating the X-ray signal with at least two radio frequency (RF) modulation signals to form a modulated X-ray signal. The modulated X-ray signal is directed toward a target material. A backscatter signal is received from the target material, and the backscatter signal includes harmonic components generated by the target material in response to receiving the modulated X-ray signal. Based at least in part on the harmonic components, a characteristic of the target material is identified.

In one embodiment, the characteristic of the target material is identified by determining a signature based on the harmonic components. The signature is compared to a plurality of known signatures, each of which corresponds to a particular characteristic. The characteristic is identified based on a match between the signature and the plurality of known signatures.

In one embodiment, the signature is determined by consecutively detecting the backscatter signal a plurality of times during a period of time, and generating a plurality of sensor data records, each sensor data record corresponding to one of the times the backscatter signal was detected and identifying a diffraction pattern of the detected backscatter signal. The signature is determined based on a change in the diffraction patterns of detected backscatter signal identified by the plurality of sensor data records.

In one embodiment, each RF modulation signal of the at least two RF modulation signals has a frequency between about 100 kilohertz and about 100 gigahertz. A first RF modulation signal of the at least two RF modulation signals may be a harmonic frequency of a second RF modulation signal of the at least two RF modulation signals.

In one embodiment, the X-ray signal has a wavelength between about 0.0001 nanometers and about ten nanometers.

In some embodiments, the two RF modulation signals modulate an intensity of the X-ray signal, and the intensity of the X-ray signal continuously stays above zero.

In another embodiment, a system for determining a characteristic of a material in provided. The system includes an X-ray source, and a modulator configured to modulate the X-ray source with at least two RF modulation signals to form a modulated X-ray signal. A transmitter is configured to transmit the modulated X-ray signal toward a target material. The system includes a receiver that is configured to receive a backscatter signal from the target material. The backscatter signal includes harmonic components generated by the target material in response to receiving the modulated X-ray signal. A controller is configured to, based at least in part on the harmonic components, identify a characteristic of the target material.

In one embodiment, the receiver includes a scintillator and a detector array.

In another embodiment, the receiver includes a direct X-ray detector that eliminates the need for the scintillator.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Any flowcharts discussed herein are necessarily discussed in some sequence for purposes of illustration, but unless otherwise explicitly indicated, the embodiments are not limited to any particular sequence of steps. The use herein of ordinals in conjunction with an element is solely for distinguishing what might otherwise be similar or identical labels, such as "first format" and "second format," and does not imply a priority, a type, an importance, or other attribute, unless otherwise stated herein.

The embodiments relate to mechanisms for causing current to flow about molecular structures, and for detecting nonlinear movements of such molecular structures to identify characteristics of a material. In particular, many structures comprise molecules that couple to one another in a lattice structure, such as metals, semiconductors, and the like. Mechanisms exist, such as X-ray crystallography, for determining the precise shape of the lattice structure. The present embodiments relate to forming currents, such as displacement currents, in a target material that result in micro-movements of the lattice structures in the target material. Where such a molecular structure is under stress, or strain, such movements may be nonlinear. The embodiments provide mechanisms not only for generating deep displacement currents in the target material sufficient to cause a molecular structure to move, but also to detect such movements.

Figure 1:
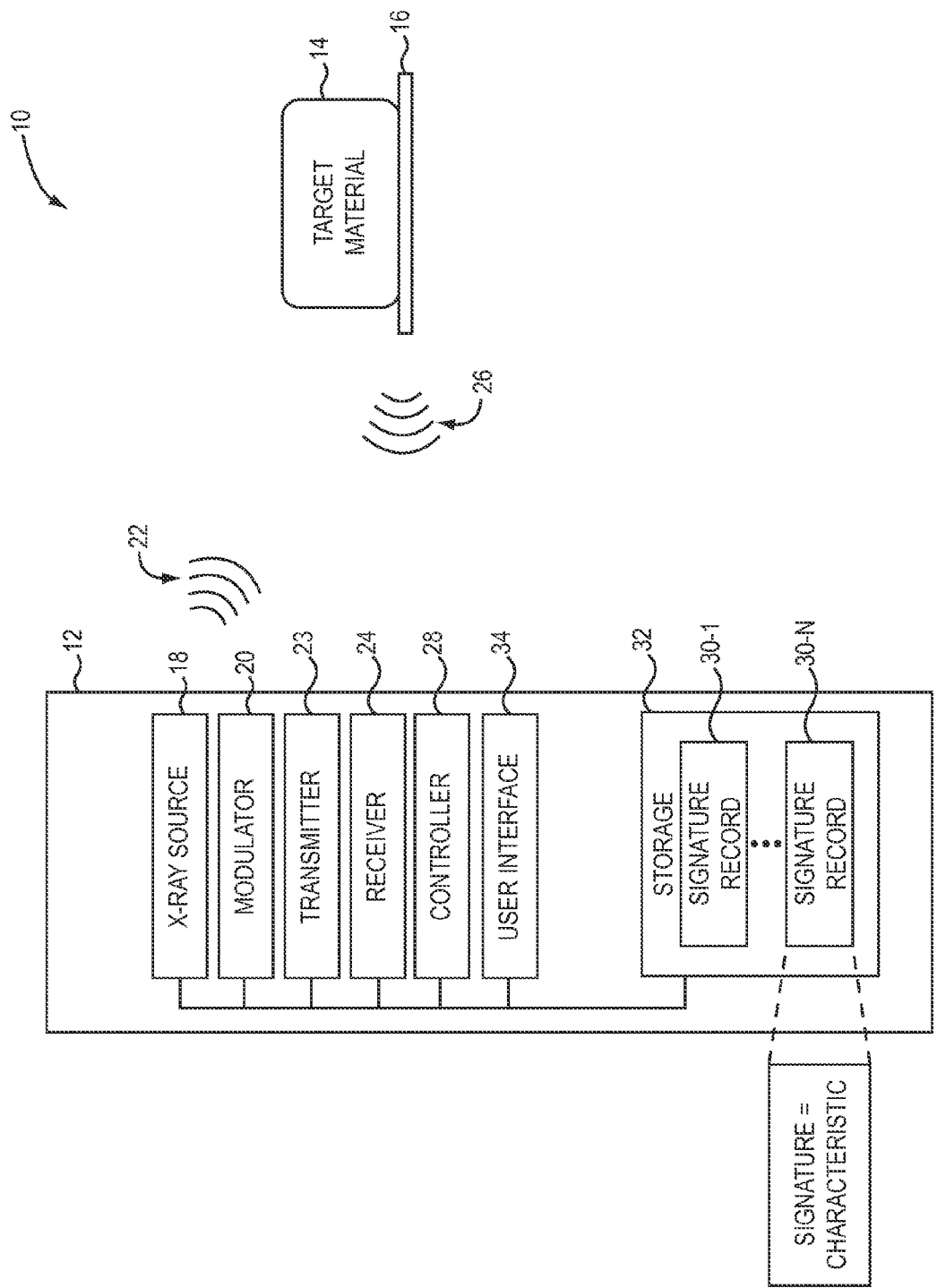
FIG. 1 is a functional block diagram of an environment in which embodiments may be practiced.

FIG. 1 is a functional block diagram of an environment 10 in which the embodiments may be practiced. The environment 10 includes a system 12 that interacts with a target material 14. The target material 14 may be free-standing, or may rest on a support 16. Although the support 16 is shown for purposes of illustration as being independent of the system 12, in some embodiments the support 16 may be integrated with the system 12. Appropriate shielding (not illustrated) may be located about the target material 14 to prevent X-ray radiation from coming into contact with a human.

The system 12 includes an X-ray source 18 which may comprise any suitable device for generating X-rays in a desired wavelength or wavelengths, including, for example, wavelengths between about 0.0001 nanometers (nm) and ten nm. Suitable X-ray sources 18 may be procured, for example, from Hamamatsu Photonics, 360 Foothill Road, Box 6910, Bridgewater, N.J. 08807. The system 12 also includes a modulator 20 which generates at least two radio frequency (RF) modulation signals, and modulates an X-ray signal with the at least two RF modulation signals to generate a modulated X-ray signal 22. In effect, the at least two RF modulation signals modulate the intensity of the X-ray signals. In some embodiments, the at least two RF modulation signals modulate the intensity of the X-ray signal such that the intensity of the X-ray signal continuously stays above zero. A transmitter 23 transmits, or otherwise directs, the modulated X-ray signal 22 toward the target material 14.

A receiver 24 receives a backscatter signal 26 in an X-ray frequency domain from the target material 14. As will be discussed in greater detail herein with reference to FIG. 2, the backscatter signal 26 includes harmonic components generated by the target material 14 in response to the receipt of the modulated X-ray signal 22. A controller 28 analyzes the backscatter signal 26, and based at least in part on the harmonic components, identifies a characteristic of the target material 14. Characteristics that may be identifiable in accordance with the present embodiments comprise any characteristic that may be identifiable based on the harmonic components in the backscatter signal 26, and include, for example, a location of stress or strain, a type of material, a logical value stored in an electronic memory, or the like.

In one embodiment, the controller 28 determines a signature based on the harmonic components in the backscatter signal 26, and accesses a plurality of predetermined signatures identified in signature records 30-1-30-N (generally, signature records 30). Each signature record 30 may comprise a predetermined signature based on harmonic components, and a particular characteristic associated with the predetermined signature. The signature records 30 may be maintained, for example, in a storage 32.

The system 12 may also include a user interface 34, which may include both a display screen and a graphical user interface to facilitate interaction with an operator.

While the various elements in the system 12 are illustrated and discussed, for purposes of illustration, as separate elements, the embodiments are not limited to any particular system design, and the functionality ascribed herein to any particular element could be combined into a single element, or any desired number of elements. In one embodiment, the controller 28 serves as a control system for the system 12, such that the functionality of each of the discussed elements operates under the control of the controller 28.

Figure 2:
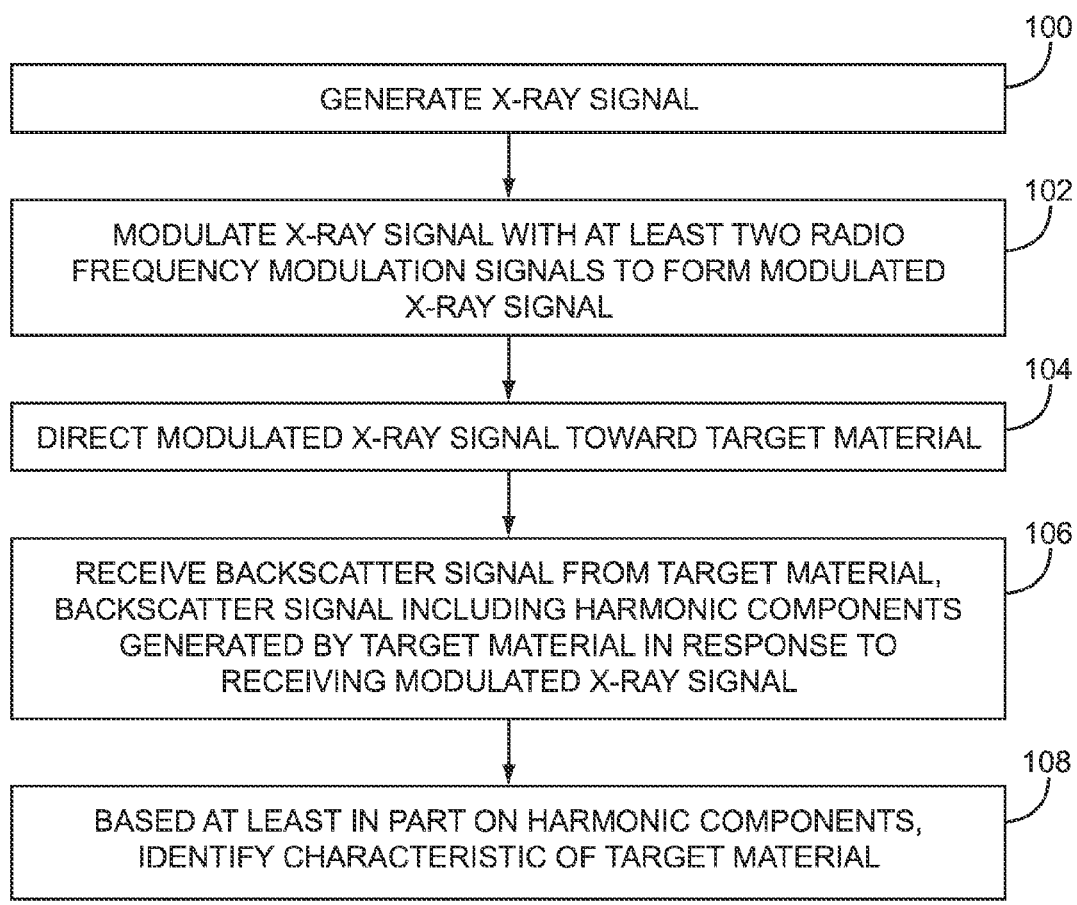
FIG. 2 is a flowchart of a method for identifying a characteristic of a target material according to one embodiment.

FIG. 2 is a flowchart of a method for identifying a characteristic of the target material 14 according to one embodiment, and will be discussed in conjunction with FIG. 1. The X-ray source 18 generates an X-ray signal (FIG. 2, block 100). The desired wavelength may differ depending on the target material 14, the receiver 24, the characteristic at issue, or based on other criteria. Preferably, the X-ray source 18 can be tuned to emit an X-ray signal in a desired wavelength. The modulator 20 modulates the X-ray signal with at least two RF modulation signals to form the modulated X-ray signal 22 (FIG. 2, block 102). While for purposes of illustration the embodiments are discussed herein in the context of two RF modulation signals, the embodiments are not limited to any particular number of RF modulation signals, and the use of three or more RF modulation signals may be desirable for various characteristics.

The RF modulation signals are in a frequency between about 100 kilohertz and about 100 gigahertz. The particular frequencies utilized may depend, at least in part, on the composition of the target material 14, the particular characteristic that is being identified, the wavelength of the modulated X-ray signal 22, or other criteria. In one embodiment, one RF modulation signal is a harmonic of the other RF modulation signal.

The modulated X-ray signal 22 is directed toward the target material 14 (FIG. 2, block 104). Due to the energy in the modulated X-ray signal 22, the receipt of the modulated X-ray signal 22 causes braking radiation (sometimes referred to as Bremsstrahlung) in the target material 14, and results in the flow of displacement currents. The displacement currents, sometimes referred to as photo currents, are modulated by both an X-ray broadband signal component of the modulated X-ray signal 22 as well as by the relatively lower frequency RF amplitude modulation of the X-ray broadband signal component. The photocurrents apply microstrains on the lattice structures of the target material 14 that may result in nonlinear motion of the lattice structures where such lattice structures are under strain or stress.

The receiver 24 receives the backscatter signal 26 from the target material 14 (FIG. 2, block 106). The backscatter signal 26 contains harmonic products of the modulation frequencies due to the nonlinear motion of the lattice structures in the target material 14. Such nonlinear motion can be represented by the fundamental frequency of the modulated X-ray signal 22, and the related harmonics of the RF modulation signals. The harmonics can generate a set of products, either lower or higher than the harmonics, that can be used to define a signature, which can then be compared to known signatures to identify a characteristic of the target material 14 (FIG. 2, block 108).

Figure 3:
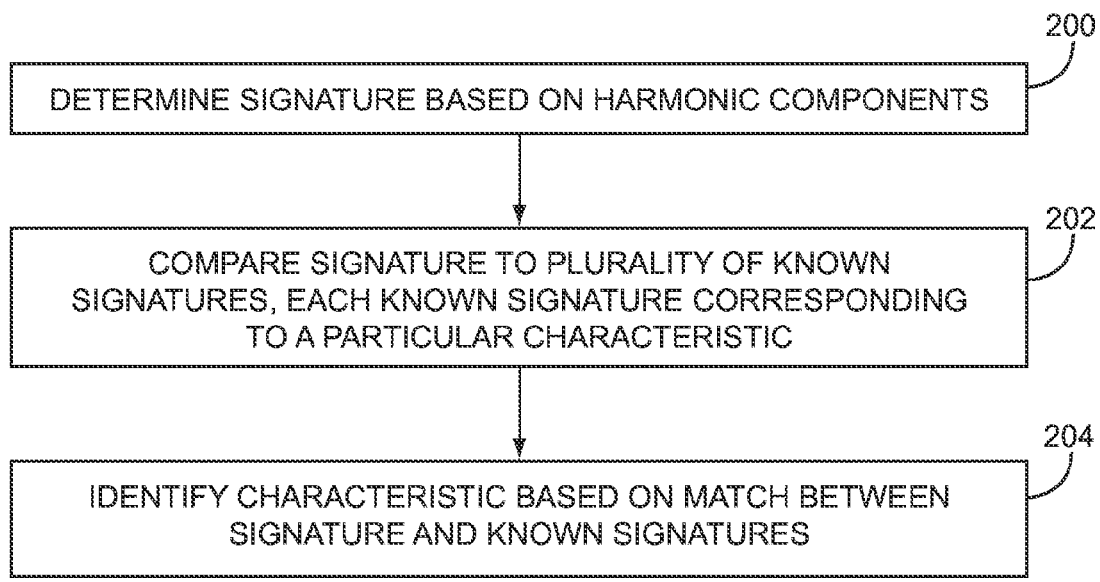
FIG. 3 is flowchart of a method for determining a characteristic of the target material based on a signature of a backscatter signal according to one embodiment.

FIG. 3 is flowchart of a method for determining a characteristic of the target material 14 based on a signature of the backscatter signal 26 according to one embodiment. As discussed above, a signature of the backscatter signal 26 may be determined based on harmonic components identified in the backscatter signal 26 (FIG. 3, block 200). For example, because the frequencies of the X-ray signal and the RF modulation signals are known, various harmonic components, such as harmonic sums and/or harmonic differences, may be examined. Examples may include $2f_1+3f_2$ and/or $3f_2-2f_1$, where $f_1$ is the frequency of one RF modulation signal and $f_2$ is the frequency of another RF modulation signal, as well as any other sum or difference products. Such products may form the basis of the signature that may be used to identify the characteristic of the target material 14. The signature records 30 may comprise signatures that comprise harmonic products from known characteristics of materials when radiated with the same or a substantially similar modulated X-ray signal 22.

The signature determined based on the harmonic components in the backscatter signal 26 may then be compared to the known signatures in the signature records 30 (FIG. 3, block 202). If a match is found between the signature and the known signatures, the characteristic corresponding to the known signature may be identified (FIG. 3, block 204).

Figure 4:
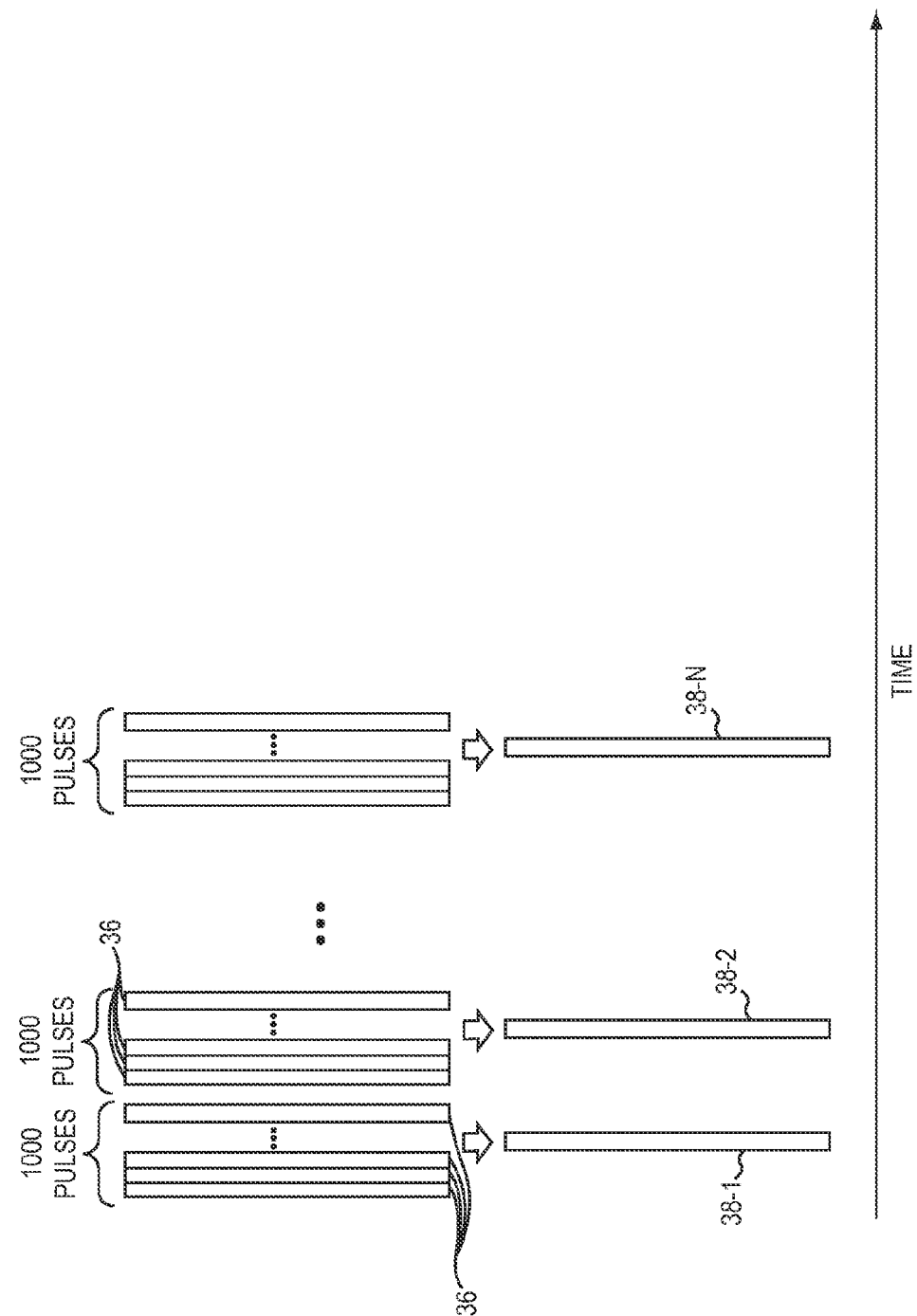
FIG. 4 is a block diagram illustrating receipt of the backscatter signal over a period of time, according to one embodiment.

FIG. 4 is a block diagram illustrating the receipt of the backscatter signal 26 over a period of time, in a frequency domain, according to one embodiment. FIG. 4 will be discussed in conjunction with FIG. 1. The modulated X-ray signal 22 may have a particular pulse rate. For example, the modulated X-ray signal 22 may be modulated by two sinusoidal signals, $f_1$ and $f_2$, and the resulting modulation waveform is the superposition of the $f_1$ and $f_2$ sinusoidal signals at their respective modulation amplitudes. The modulated x-ray signal 22 can be modulated as a series of pulses, wherein the superposition of the $f_1$ and $f_2$ sinusoidal signals creates a pulse train with high and low pulse amplitudes set by the superposition.

Assume, for purposes of illustration, that the pulse rate of the modulated X-ray signal 22 is three gigahertz. The receiver 24, in some embodiments, may consecutively detect the backscatter signal 26 for a predetermined number of pulses, such as 1000 pulses. Each detection 36 corresponds to one pulse, and generates data that identifies a diffraction pattern of the received backscatter signal 26. The 1000 pulses received may then be integrated to form a sensor data record 38, which may, in some contexts, be referred to as a range bin. The period of time during which the 1000 pulses are received may be referred to as an integration timespan. In this example, this would result in a three megahertz detection rate, with relatively high quality signal-to-noise. This process, for example, is repeated every integration timespan, in this example every 1000 pulses, such that the sensor data record 38-2 reflects a diffraction pattern that is three microseconds later in time than the diffraction pattern reflected in the sensor data record 38-1. The sensor data records 38 may then be analyzed for changes in the diffraction patterns at desired harmonic frequencies to determine a signature. Such changes in diffraction patterns may reflect changes in the lattice structure of the target material 14 that occurred in response to the receipt of the modulated X-ray signal 22.

In this example, wherein the pulse train is integrated for 1000 pulses at three gigahertz, the modulated X-ray signal 22 is held on for a period of time corresponding to 1000 pulses at three gigahertz, and then the signal pattern is repeated. Thus, the target material 14 is in effect illuminated by the modulated X-ray signal 22 at three gigahertz, and at one-and-one-half megahertz. A time series analysis of the backscatter signal 26 from the received modulated X-ray signal 22 at the target material 14 over time periods greater than twice the one-and-one-half megahertz modulation cycle will enable detection of harmonic components of the three gigahertz X-ray broadband signal and the one-and-one-half megahertz modulation signals.

It should be apparent that the embodiments are not limited to any particular pulse rate, or integration timespan, and that different pulse rates and integration timespan may be useful depending on, for example, the particular characteristics being sought. For example, the use of a laser driven X-ray source may permit, for example, 100 gigahertz pulse rates, with even tighter range bins than discussed above, which facilitates higher integrations of pulses and/or change detection rates.

Figure 5:
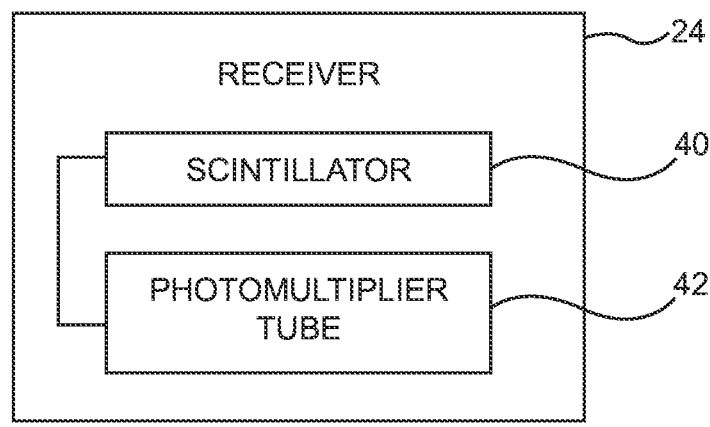
FIG. 5 is a block diagram of a receiver according to one embodiment.

FIG. 5 is a block diagram of the receiver 24 according to one embodiment. In this embodiment, the receiver 24 includes a scintillator 40 and a photomultiplier tube 42. The photomultiplier tube 42 may also include an integrated microchannel plate. Suitable scintillators 40 and photomultiplier tubes 42 may be available from a number of sources, including, for example, Hamamatsu Photonics referenced above. The use of a scintillator and photomultiplier tube may be suitable for both soft X-rays as well as hard X-rays, and the use of the scintillator may facilitate relatively high response, such as a 100 picosecond (ten gigahertz) fluorescence response.

Figure 6:
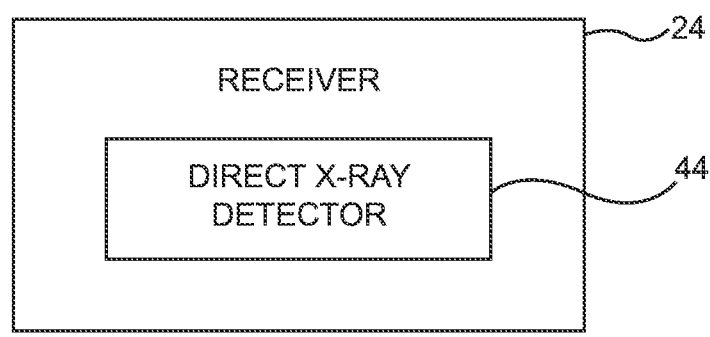
FIG. 6 is a block diagram of a receiver according to another embodiment.

FIG. 6 is a block diagram of the receiver 24 according to another embodiment. In this embodiment, the receiver 24 includes a direct X-ray detector 44. This embodiment may be suitable for soft X-rays, and trades higher frequency (i.e., "hard") X-ray resolution for a substantially smaller receiver 24 than the embodiment discussed above with regard to FIG. 5.

In some embodiments, the receiver 24 may include a sensor, or detector, that has an array of pixel elements. In other embodiments, the receiver 24 may include a sensor, or detector, that has a relatively small number of sensors, or detector elements, and in some embodiments, only a single detector element may be utilized. In such embodiments, the receiver 24 may be carried on a scanner, or scan drive, such that a single detector element may be moved to receive the backscatter signal 26 from different locations of the target material 14 directly, or, when used in conjunction with a scintillator, the scan drive may move the detector with respect to the scintillator.

Figure 7:
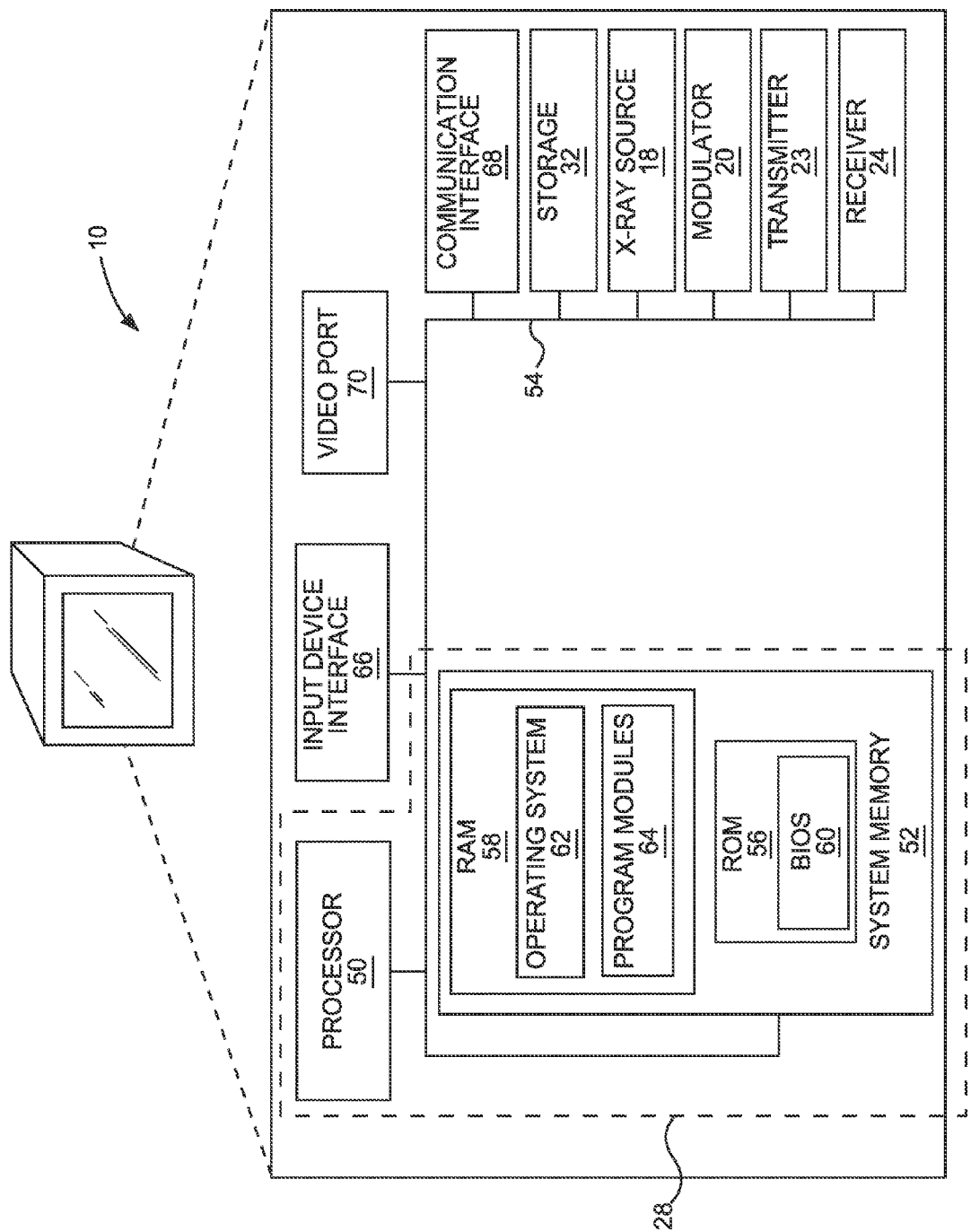
FIG. 7 is a block diagram of the system illustrated in FIG. 1 according to another embodiment.

FIG. 7 is a block diagram illustrating the system 12 according to another embodiment. The system 12 may comprise one or more separate devices that cooperate functionally as described above. The system 12 may include a processor 50, a system memory 52, and a system bus 54, in one embodiment. The system bus 54 may provide an interface for system components including, but not limited to, the system memory 52 and the processor 50. The processor 50 can be any commercially available or proprietary processor. Dual microprocessors and other multi-processor architectures may also be employed as the processor 50.

The system bus 54 may be one or more of any of several types of communication links that may further interconnect to a memory bus (with or without a memory controller), a peripheral bus, and/or a local bus using any of a variety of commercially available bus architectures. The system memory 52 may include non-volatile memory 56 (e.g., read only memory (ROM), erasable programmable read only memory (EPROM), electrically erasable programmable read only memory (EEPROM), etc.) and/or volatile memory 58 (e.g., random access memory (RAM)). A basic input/output system (BIOS) 60 may be stored in the non-volatile memory 56, and can include the basic routines that help to transfer information between elements within the system 12. The volatile memory 58 may also include a high-speed RAM, such as static RAM for caching data.

The system 12 may further include a computer-readable storage 32, which may comprise, for example, an internal hard disk drive (HDD) (e.g., enhanced integrated drive electronics (EIDE) or serial advanced technology attachment (SATA)), HDD (e.g., EIDE or SATA) for storage, flash memory, or the like. The computer-readable storage 32 and other drives, associated with computer-readable and computer-usable media, provide non-volatile storage of data, data structures, computer-executable instructions, and the like. Although the description of computer-readable media above refers to an HDD, it should be appreciated by those skilled in the art that other types of media which are readable by a computer, such as Zip disks, magnetic cassettes, flash memory cards, cartridges, and the like, may also be used in the exemplary operating environment, and further, that any such media may contain computer-executable instructions for performing novel methods of the disclosed architecture.

A number of modules can be stored in the computer-readable storage 32 and in the volatile memory 58, including an operating system 62 and one or more program modules 64, which may implement the functionality described herein in part, including, for example, functionality associated with the determination of signatures and identification of a characteristic of the target material 14 based on such signatures. It is to be appreciated that the embodiments can be implemented with various commercially available operating systems 62 or combinations of operating systems 62.

A portion of the embodiments may be implemented as a computer program product stored on a transitory or non-transitory computer-usable or computer-readable storage medium, such as the computer-readable storage 32, which includes complex programming instructions, such as complex computer-readable program code, configured to cause the processor 50 to carry out the steps described herein. Thus, the computer-readable program code can comprise software instructions for implementing the functionality of the embodiments described herein when executed on the processor 50. The processor 50, in conjunction with the program modules 64 in the volatile memory 58, may serve as the controller 28 for the system 12 that is configured to, or adapted to, implement the functionality described herein.

A user, such as an operator, may be able to enter commands and information into the system 12 through one or more input devices, such as, for example, a keyboard (not illustrated), a pointing device such as a mouse (not illustrated), or a touch-sensitive surface (not illustrated). Other input devices may include a microphone, an infrared (IR) remote control, a joystick, a game pad, a stylus pen, or the like. These and other input devices may be connected to the processor 50 through an input device interface 66 that is coupled to the system bus 54, but can be connected by other interfaces such as a parallel port, an Institute of Electrical and Electronic Engineers (IEEE) 1394 serial port, a Universal Serial Bus (USB) port, an IR interface, and the like.

The system 12 may also include a communication interface 68 suitable for communicating with a network, or for communicating with one or more of the other elements discussed herein, such as, for example, the X-ray source 18, modulator 20, transmitter 23 or receiver 24. The system 12 may also include a video port 70 interfacing with a display that provides information to the operator via, for example, the user interface 34.

The embodiments have applicability in a wide variety of applications, including, for example mining, and nuclear quadrupole resonance sensing.

Those skilled in the art will recognize improvements and modifications to the preferred embodiments of the present disclosure. All such improvements and modifications are considered within the scope of the concepts disclosed herein and the claims that follow.

What is claimed is:

1. A method for identifying a characteristic of a material, comprising:
    generating an X-ray signal;
    modulating the X-ray signal with at least two radio frequency (RF) modulation signals to form a modulated X-ray signal;
    directing the modulated X-ray signal toward a target material;
    receiving a backscatter signal from the target material, the backscatter signal including harmonic components generated by the target material in response to receiving the modulated X-ray signal; and
    based at least in part on the harmonic components, identifying a characteristic of the target material.

2. The method of claim 1, wherein identifying the characteristic of the target material comprises:
    determining a signature based on the harmonic components;
    comparing the signature to a plurality of known signatures, each of the plurality of known signatures corresponding to a particular characteristic; and
    identifying the characteristic based on a match between the signature and the plurality of known signatures.

3. The method of claim 2, wherein determining the signature based on the harmonic components comprises:
    consecutively detecting the backscatter signal a plurality of times during a period of time, and generating a plurality of sensor data records, each sensor data record corresponding to one of the times the backscatter signal was detected and identifying a diffraction pattern of detected backscatter signal; and
    determining the signature based on a change in the diffraction patterns of the detected backscatter signal identified by the plurality of sensor data records.

4. The method of claim 3, wherein the diffraction pattern of the detected backscatter signal changes during the period of time based on a movement of a lattice structure in the target material in response to receipt of the modulated X-ray signal.

5. The method of claim 3, wherein each sensor data record comprises an integration of a plurality of detections of the backscatter signal over an integration timespan.

6. The method of claim 1, wherein the characteristic comprises one of a type of material, a binary value stored in a semiconductor memory, a region under stress, and a region under strain.

7. The method of claim 1, wherein each RF modulation signal of the at least two RF modulation signals has a frequency between about 100 kilohertz and about 100 gigahertz.

8. The method of claim 7, wherein a first RF modulation signal of the at least two RF modulation signals is a harmonic frequency of a second RF modulation signal of the at least two RF modulation signals.

9. The method of claim 1, wherein the X-ray signal has a wavelength between about 0.0001 nanometers and about ten nanometers.

10. The method of claim 1, wherein the two RF modulation signals modulate an intensity of the X-ray signal, and wherein the intensity of the X-ray signal continuously stays above zero.

11. A system for determining a characteristic of a material, comprising:
- an X-ray source;
- a modulator configured to modulate the X-ray source with at least two radio frequency (RF) modulation signals to form a modulated X-ray signal;
- a transmitter configured to transmit the modulated X-ray signal toward a target material;
- a receiver configured to receive a backscatter signal from the target material, the backscatter signal including harmonic components generated by the target material in response to receiving the modulated X-ray signal; and
- a controller configured to, based at least in part on the harmonic components, identify a characteristic of the target material.

12. The system of claim 11, wherein the receiver comprises a scintillator and a detector array.

13. The system of claim 11, wherein the receiver comprises a direct X-ray detector.

14. The system of claim 11, wherein to identify the characteristic of the target material, the controller is configured to:
- determine a signature based on the harmonic components;
- compare the signature to a plurality of known signatures, each of the plurality of known signatures corresponding to a particular characteristic; and
- identify the characteristic based on a match between the signature and the plurality of known signatures.

15. The system of claim 14, wherein to determine the signature based on the harmonic components, the controller is configured to:
- consecutively detect the backscatter signal a plurality of times during a period of time, and generate a plurality of sensor data records, each sensor data record corresponding to one of the times the backscatter signal was detected and identifying a diffraction pattern of the detected backscatter signal; and
- determine the signature based on a change in the diffraction patterns of the detected backscatter signal identified by the plurality of sensor data records.

16. The system of claim 15, wherein the diffraction pattern of the detected backscatter signal changes during the period of time based on a movement of a lattice structure in the target material in response to receipt of the modulated X-ray signal.

17. The system of claim 15, wherein each sensor data record comprises an integration of a plurality of detections of the backscatter signal over an integration timespan.

18. The system of claim 11, wherein the characteristic comprises one of a type of material, a binary value stored in a semiconductor memory, a region under stress, and a region under strain.

19. The system of claim 11, wherein each RF modulation signal of the at least two RF modulation signals has a frequency between about 100 kilohertz and about 100 gigahertz.

20. The system of claim 19, wherein a first RF modulation signal of the at least two RF modulation signals is a harmonic frequency of a second RF modulation signal of the at least two RF modulation signals.

21. The system of claim 11, wherein the X-ray signal has a wavelength between about 0.0001 nanometers and about ten nanometers.

22. The system of claim 11, wherein the two RF modulation signals modulate an intensity of the X-ray signal, and wherein the intensity of the X-ray signal continuously stays above zero.

* * * * *